(12) United States Patent
Reznik et al.

(10) Patent No.: US 10,816,678 B2
(45) Date of Patent: Oct. 27, 2020

(54) TILEABLE BLOCK DETECTORS FOR SEAMLESS BLOCK DETECTOR ARRAYS IN POSITRON EMISSION MAMMOGRAPHY

(71) Applicant: Lakehead University, Thunder Bay, Ontario (CA)

(72) Inventors: Alla Reznik, Shuniah (CA); Oleksandr Bubon, Thunder Bay (CA); Aram Teymurazyan, Regina (CA)

(73) Assignee: RADIALIS INC., Ontario (CA)

( * ) Notice: Subject to any disclaimer, the term of this patent is extended or adjusted under 35 U.S.C. 154(b) by 120 days.

(21) Appl. No.: 16/080,064

(22) PCT Filed: Feb. 23, 2017

(86) PCT No.: PCT/CA2017/050228
§ 371 (c)(1),
(2) Date: Aug. 27, 2018

(87) PCT Pub. No.: WO2017/143442
PCT Pub. Date: Aug. 31, 2017

(65) Prior Publication Data
US 2019/0064367 A1    Feb. 28, 2019

Related U.S. Application Data

(60) Provisional application No. 62/300,256, filed on Feb. 26, 2016.

(51) Int. Cl.
*G01T 1/164* (2006.01)
*G01T 1/202* (2006.01)
(Continued)

(52) U.S. Cl.
CPC ............ *G01T 1/1644* (2013.01); *A61B 6/502* (2013.01); *G01T 1/164* (2013.01); *G01T 1/202* (2013.01); *G01T 1/2018* (2013.01); *A61B 6/037* (2013.01)

(58) Field of Classification Search
None
See application file for complete search history.

(56) References Cited

U.S. PATENT DOCUMENTS 6,553,092 B1 * 4/2003 Mattson ................ G01T 1/2018
250/370.11
2001/0040219 A1    11/2001 Cherry
(Continued)

FOREIGN PATENT DOCUMENTS

EP          2746816      6/2014
WO       2013040646      3/2013

OTHER PUBLICATIONS

International Search Report and Written Opinion, dated May 16, 2017, 6 pages.

(Continued)

*Primary Examiner* — Edwin C Gunberg
(74) *Attorney, Agent, or Firm* — Quarles & Brady LLP

(57) ABSTRACT

Described here are tileable block detectors for use in nuclear medicine applications, such as in positron emission tomography ("PET") systems and positron emission mammography ("PEM") systems. The block detectors described here are four-side tileable such that seamless arrays of block detectors can be constructed for use in PET or PEM systems. When so arrayed, the block detectors allow for a full-size seamless detector that achieves full coverage of an object (e.g., a gently immobilized breast), improves data collection, and enables high-resolution imaging with a significantly lower radiation dose than with other currently available PEM systems.

14 Claims, 2 Drawing Sheets

(51) Int. Cl.
   *G01T 1/20*       (2006.01)
   *A61B 6/00*       (2006.01)
   *A61B 6/03*       (2006.01)

(56) References Cited

U.S. PATENT DOCUMENTS

| | | | |
|---|---|---|---|
| 2006/0060823 A1* | 3/2006 | Cooke | C09K 11/7774 |
| | | | 252/301.36 |
| 2007/0209581 A1 | 9/2007 | Ferrand | |
| 2008/0073542 A1* | 3/2008 | Siegel | G01T 1/1644 |
| | | | 250/368 |
| 2014/0064446 A1 | 3/2014 | Wear | |

OTHER PUBLICATIONS

Berg WA, et al., High-resolution fluorodeoxyglucose positron emission tomography with compression ("positron emission mammography") is highly accurate in depicting primary breast cancer. Breast J. Jul.-Aug. 2006;12(4):309-23. PMID: 16848840.

Hruska, CB, et al., Nuclear imaging of the breast: Translating achievements in instrumentation into clinical use. Medical Physics, 40, 050901 (2013), doi:10.1 118/1.4802733.

Hendrick RE. Radiation doses arid cancer risks from breast imaging studies. Radioloay. Oct. 2010:257(1):246-53, doi: 10.1148/radiol. 10100570. PMID: 20736332.

* cited by examiner

TILEABLE BLOCK DETECTORS FOR SEAMLESS BLOCK DETECTOR ARRAYS IN POSITRON EMISSION MAMMOGRAPHY

CROSS-REFERENCE TO RELATED APPLICATIONS

This application represents the national stage entry of International Application PCT/CA2017/050228, filed Feb. 23, 2017, which claims benefit of and priority to U.S. Provisional Patent Application 62/300,256, filed Feb. 26, 2016, which is incorporated herein by reference in its entirety for all purposes.

BACKGROUND

The field of the present disclosure is positron emission tomography ("PET"). More particularly, the present disclosure relates to radiation detector arrays for use in PET systems, including positron emission mammography ("PEM") systems.

Women with highly dense breast tissue suffer from both higher risk of breast cancer and lower sensitivity of mammographic screening. PEM offers a potential solution for these women who have an increased need for effective screening. If the radiotracer dose is lowered sufficiently, PEM could be an effective screening tool, especially in high-risk women with dense breasts for whom mammography has unacceptably low sensitivity. Currently, a PEM dose of 370 MBq (10 mCi) of fludeoxyglucose ("FDG") has a lifetime equivalent risk that is 23 times greater than digital mammography, which severely limits its clinical acceptance.

Thus, there is a need to provide a PEM system that is capable of generating images using a significantly reduced dose administered to the subject while maintaining high sensitivity and specificity in a screening context.

In some PEM systems, one or more large block detectors are scanned over the subject's breast. Although these systems may be able to operate at lower dose to the subject, the scanning technique reduces the amount of time that the sensors are exposed to a particular breast region, thereby reducing the sensitivity of the system. It is also possible for other measurement errors to be introduced because of the scanning motion.

Other PEM systems use a circular array of gamma ray detectors. In these systems, the subject lies prone and the breast hangs into the ring of the array. The ring design allows for greater sensitivity and faster scanning times, but is less able to accommodate differences in breast sizes compared to other systems and has poorer imaging of lesions near the chest wall.

It would be desirable to have a PEM system that uses a detector that is large enough to cover the entire breast with slight compression and without needing to move the detector. Such a stationary system would be able to collect more signal while using a lower radio-tracer dose.

SUMMARY OF THE DISCLOSURE

The present disclosure addresses the aforementioned drawbacks by providing a block detector for use in a positron emission tomography ("PET") system. The block detector includes a scintillator array comprising a plurality of scintillator crystals, a photodetector comprising a plurality of photodetector elements, and a light guide that is optically coupled to the scintillator array and the photodetector. The photodetector has a surface area smaller than a surface area of the scintillator array such that the scintillator array defines an overhang relative to the photodetector. The light guide has a first surface facing and optically coupled to a bottom surface of the scintillator array, and a second surface facing and optically coupled to an active surface of the photodetector. The first surface of the light guide has a first surface area and the second surface of the light guide has a second surface area that is smaller than the first surface area.

It is another aspect of the present disclosure to provide an array of block detectors for use in a PET system. The array of block detectors includes a plurality of block detectors, where each block detector includes a scintillator array comprising a plurality of scintillator crystals, a photodetector comprising a plurality of photodetector elements, and a light guide that is optically coupled to the scintillator array and the photodetector. The photodetector has a surface area smaller than a surface area of the scintillator array such that the scintillator array defines an overhang relative to the photodetector. The light guide has a first surface facing and optically coupled to a bottom surface of the scintillator array, and a second surface facing and optically coupled to an active surface of the photodetector. The plurality of block detectors are arranged in an array such that the scintillator arrays in adjacent block detectors meet at an interface with substantially no gap therebetween and photodetectors in adjacent block detectors are separated by a gap defined by the overhang.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are tileable block detectors for use in nuclear medicine applications, such as in positron emission tomography ("PET") systems, and in some specific examples positron emission mammography ("PEM") systems. The tileable block detectors are one component in such PET or PEM systems. Advantageously, the block detectors described here are four-side tileable such that seamless arrays of block detectors can be constructed for use in PET or PEM systems. When so arrayed, the block detectors allow for a full-size seamless detector that achieves full coverage of an object (e.g., a gently immobilized breast), improves data collection, and enables high-resolution imaging with a significantly lower radiation dose than with other currently available PEM systems.

PET systems often utilize block detectors to detect gamma rays. These block detectors include a photodetector (e.g., photomultiplier tubes (PMTs) or solid-state photodetectors) that is optically coupled to a scintillator, such as a scintillating crystal. PET block detectors use a light sharing technique to define the position where gamma rays interacted with the scintillator more efficiently and precisely. For instance, to achieve better spatial resolution, an array of scintillator crystals (e.g., a pixelated scintillating crystal) is used. Such arrays of scintillator crystals are optically coupled to the photodetector through a light guide to distribute light to an array of photodetectors.

The block detectors described here are designed to eliminate gaps between adjacent detectors when they are arrayed into larger structures, such as 3×3 arrays, 4×4 arrays, 3×4 arrays, and so on. When block detectors using solid-state photodetectors are arrayed, it is a common problem to have gaps between the scintillators in the block detectors. The block detectors described here are designed to address and overcome this problem.

Figure 1:
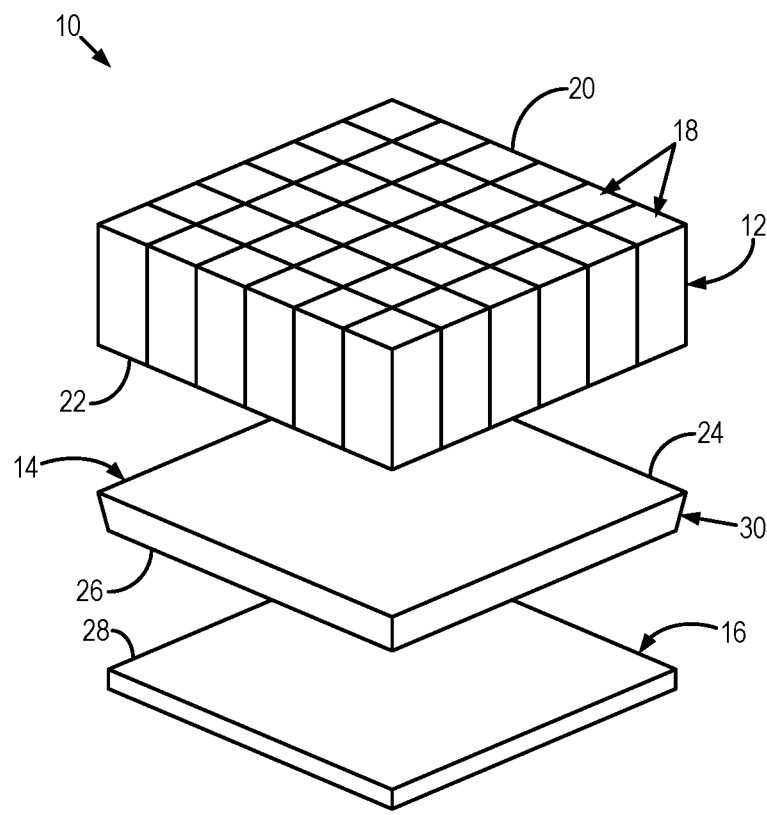
FIG. 1 is an exploded view of an example four-way tileable block detector.
Figure 2:
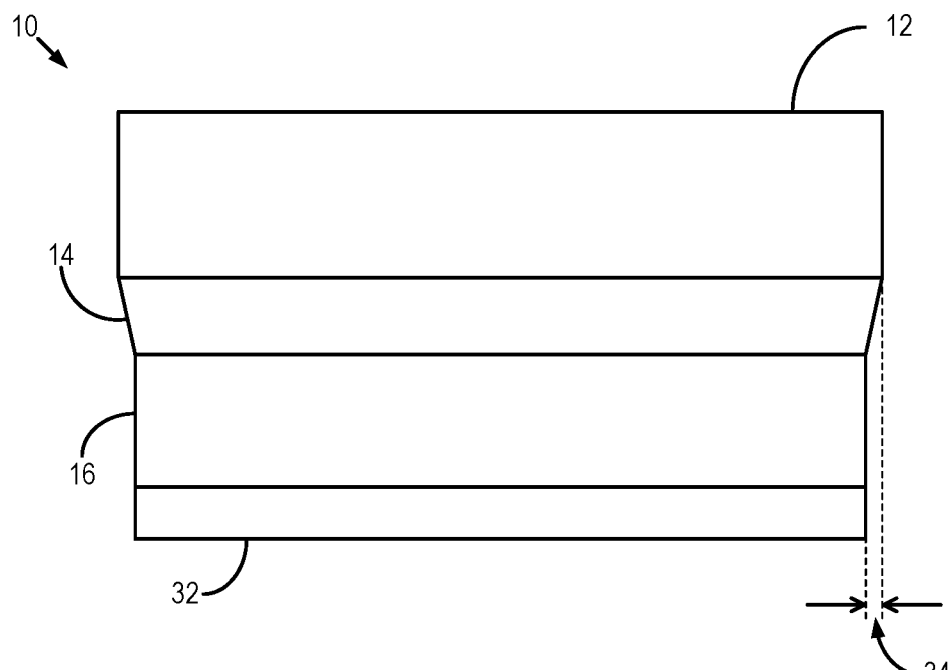
FIG. 2 is a side view of an example four-way tileable block detector.

FIGS. 1 and 2 show an example of a tileable block detector 10 for use in PET systems, including PEM systems. Each block detector 10 generally includes a scintillator array 12, a light guide 14, and a photodetector 16. Preferably, the photodetector 16 is a solid-state photodetector having an array of photodetector elements, or pixels. Example solid-state photodetectors include silicon photomultiplier ("SiPM"), avalanche photodiodes ("APD"), and digital SiPM without light guides. Advantageously, the block detector 10 is designed to be a four-way tileable detector, such that seamless arrays of block detectors 10 can be constructed, including 3×3 arrays, 4×4 arrays, 3×4 arrays, and so on.

In general, the block detector 10 is constructed such that the scintillator array 12 has a larger surface area than the light guide 14, photodetector 16, and front end electronics 32 coupled to the photodetector 16. Thus, the surface area of the block detector 10 is defined by the size of the scintillator array 12 used. More particularly, the scintillator array 12 is dimensioned to define an overhang 34 over the photodetector 16, which allows the block detectors 10 to be seamlessly tileable. As one example, the overhang 34 can be about 500-600 μm. In some embodiments, the overall thickness of the block detector 10 is about 35 mm or less, which allows the block detector 10 to be placed very close to the chest wall such that images of the chest can be acquired to detect lesions therein.

The scintillator array 12 generally comprises an array of scintillator crystals 18. The scintillator array 12 can be constructed as a cut-block scintillator, or as a reflector-block scintillator. As one example, the scintillator crystals 18 can be LYSO:Ce crystals; however, other inorganic crystals can also be used, including crystals composed of CsF, NaI(Tl), $LaCl_3(Ce)$, BGO, $CaF_2(Eu)$, YAG(Ce), and so on. In some other embodiments, the scintillator crystals 18 can be organic or ceramic crystals. In still other embodiments, the scintillator array 12 can include arrays of other non-crystal scintillators, including those based on organic liquids, or fluorescent emitters.

The scintillator array 12 extends from a top surface 20 to a bottom surface 22. The light guide 14 is positioned between the scintillator array 12 and the photodetector 16 so as to optically couple the scintillator array 12 to the photodetector 16. Radiation (e.g., 511 keV photons) impinging on the top surface 20 of the scintillator array 12 is absorbed by the scintillator array 12, in response to which light (e.g., visible light) is emitted from the scintillator array 12. The emitted light is transmitted to the photodetector 16 by way of the light guide 14.

The light guide 14 has a first surface 24 facing and optically coupled to the bottom surface 22 of the scintillator array 12, and a second surface 26 facing and optically coupled to an active surface 28 of the photodetector 16. Preferably, the light guide 14 is dimensioned such that the first surface 24 has the same surface area as the bottom surface 22, and the second surface 26 has the same surface area as the active surface 28 of the photodetector 16. The light guide 14 can be composed of any suitable type of glass (e.g., borosilicate, fused silica, lead glass) as well as any suitable transparent plastic (e.g., acrylic, polycarbonate, polystyrol), and can be constructed using an accurate repeatable polishing or thermal etching technique to maintain high quality of the light guide.

Light impinging on the first surface 24 of the light guide is distributed from one pixel (e.g., the crystal 18 from which the light was emitted) of the scintillator array 12 between many pixels of the photodetector 16. Using the light guide 14 thus allows for fewer electronic readout channels while at the same time yielding very accurate results in determining the position where incident radiation (e.g., 511 keV photons) hit the scintillator array 12. Furthermore, by keeping the surface area of the first surface 24 large, the light guide 14 allows the block detector 10 to maintain the same level of photodetection efficiency as in the case of no overhang 34 existing between the scintillator array 12 and the photodetector 16.

The light guide 14 is also generally shaped so its first surface 24 has a larger surface area than the surface area of the second surface 26 of the light guide 14. In some embodiments, the edges 30 of the light guide 14 are beveled to slope inward from the first surface 24 to the second surface 26 of the light guide 14. As other examples, the edges 30 of the light guide can be generally convex or concave. Preferably, the edges 30 are coated with a reflective compound to prevent scintillation light loss and maintain high light collection efficiency. Whenever a gamma ray from positron annihilation interacts with the scintillator array 12 near the edge of the scintillator array 12, this reflective coating directs most of the light to the photodetector 16.

Light emitted by the scintillator array 12 and impinging on the photodetector 16 by way of the light guide 14 creates electrical signals that are readout as data from the photodetector 16 by front-end electronics 32. This data is communicated to a computer system for image reconstruction and other processing. As mentioned above, the block detector 10 provides better spatial resolution by using a scintillator array 12 that includes an array of scintillating crystals 18 and a photodetector 16 that includes an array of photodetector elements. In this configuration, the light guide 14 distributes the light emitted from a scintillator crystal 18 in the scintillator array 12 to the array of photodetector elements. Anger logic math can then be used to determine the position of gamma ray interactions with the scintillator array 12.

Figure 3:
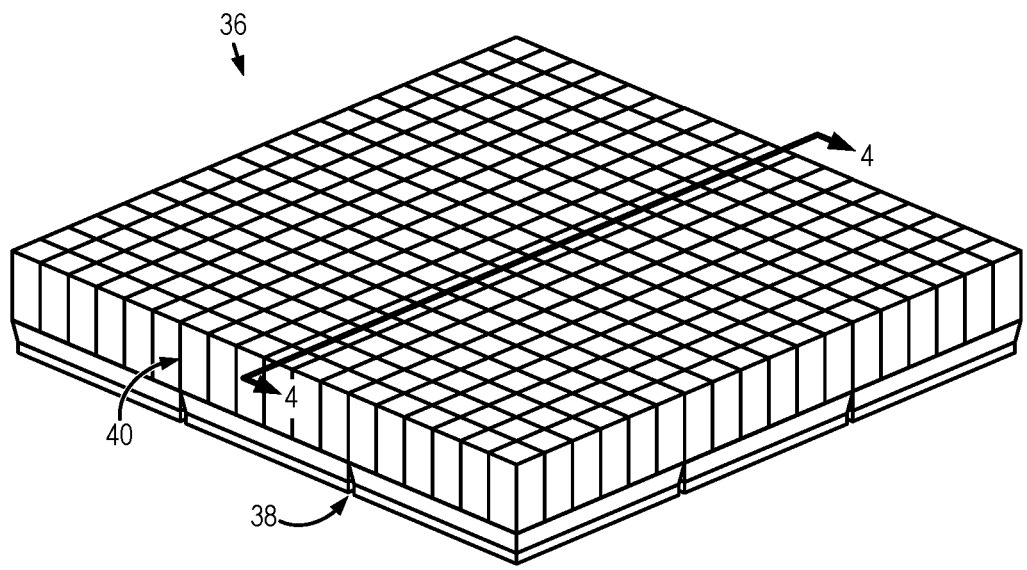
FIG. 3 shows a seamless array of four-way tileable block detectors.
Figure 4:
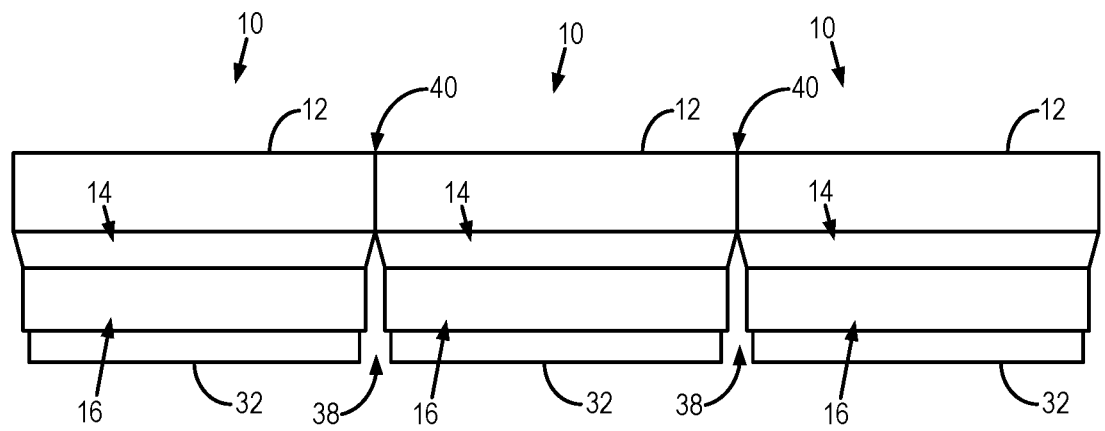
FIG. 4 is a cross-sectional view of the seamless array of four-way tileable block detectors of FIG. 3.

An example array 36 of block detectors 10 is shown in FIG. 3 with a corresponding cross-section of the array 36 shown in FIG. 4. Because the block detectors 10 can be seamlessly tiled, the block detector array 36 provides an imaging zone with virtually no dead zones between the block detectors 10. As a result of this seamless construction, less radiation will escape the block detector array 36 due to gaps that are present between block detectors in other currently available devices. Although a 3×3 array is illustrated in FIG. 2, because the block detectors 10 are four-way tileable, any suitable configuration of arrayed block detectors 10 can be constructed, including 3×4 arrays, 4×4 arrays, and so on.

As one example, each block detector 10 can have dimensions of 57.66 mm by 57.66 mm (i.e., the scintillator array 12 is dimensioned to be 57.66 mm by 57.66 mm), such that a 3×3 array 36 of block detectors 10 would have an imaging zone of 17.3 cm by 17.3 cm. It will be appreciated by those skilled in the art, however, that different sized block detectors 10 can also be constructed.

When arrayed, the overhang 34 of the block detectors 10 define a gap 38 between the photodetectors 16 in adjacent block detectors 10, while allowing a seamless interface 40 between the scintillator arrays 12 in adjacent block detectors 10. Advantageously, the gap 38 between photodetectors 16 can act as a convective channel that allows airflow around the photodetectors 16 and front end electronics 32, thereby providing cooling of these electronic components of the block detector 10. As mentioned above, the overhang 34 is generally dimensioned to be about 500-600 nm and, thus, the gap 38 between photodetectors 16 is about 1000-1200 nm.

The present disclosure has described one or more preferred embodiments, and it should be appreciated that many equivalents, alternatives, variations, and modifications, aside from those expressly stated, are possible and within the scope of the invention.

The invention claimed is:

1. A block detector for use in a positron emission tomography (PET) system, comprising:
   a scintillator array comprising a plurality of scintillator crystals;
   a photodetector comprising a plurality of photodetector elements and having a surface area smaller than a surface area of the scintillator array such that the scintillator array defines an overhang relative to the photodetector;
   a light guide optically coupled to the scintillator array and photodetector, the light guide having a first surface facing and optically coupled to a bottom surface of the scintillator array and a second surface facing and optically coupled to an active surface of the photodetector;
   wherein the first surface of the light guide has a first surface area and the second surface of the light guide has a second surface area that is smaller than the first surface area; and
   wherein the light guide is dimensioned to optically couple a single scintillator crystal in the scintillator array to a plurality of photodetector elements in the photodetector, thereby enabling light sharing between photodetector elements.

2. The block detector as recited in claim 1, wherein the light guide has a beveled edge that slopes inward from the first surface to the second surface.

3. The block detector as recited in claim 2, wherein the beveled edge is coated in a reflective material that reflects light inside the light guide back into the light guide.

4. The block detector as recited in claim 1, wherein the bottom surface of the scintillator array has a same size and shape as the first surface of the light guide, and the active surface of the photodetector has a same size and shape as the second surface of the light guide.

5. The block detector as recited in claim 1, wherein the overhang is in a range of about 500 micrometers to about 600 micrometers.

6. The block detector as recited in claim 1, further comprising front end electronics coupled to the photodetector so as to receive data from the photodetector as electrical signals generated when light impinges on photodetector elements in the photodetector, the front end electronics having a surface area smaller than the first surface area of the light guide.

7. The block detector as recited in claim 1, wherein the photodetector is a solid-state photodetector.

8. The block detector as recited in claim 1, wherein the scintillator crystals are LYSO:Ce crystals.

9. An array of block detectors for use in a positron emission tomography (PET) system, comprising:
   a plurality of block detectors, each block detector comprising:
      a scintillator array comprising a plurality of scintillator crystals;
      a photodetector comprising a plurality of photodetector elements and having a surface area smaller than a surface area of the scintillator array such that the scintillator array defines an overhang relative to the photodetector;
      a light guide optically coupled to the scintillator array and photodetector, the light guide having a first surface facing and optically coupled to a bottom surface of the scintillator array and a second surface facing and optically coupled to an active surface of the photodetector;
      wherein the first surface of the light guide has a first surface area and the second surface of the light guide has a second surface area that is smaller than the first surface area;
   wherein the light guide is dimensioned to optically couple a single scintillator crystal in the scintillator array to a plurality of photodetector elements in the photodetector, thereby enabling light sharing between photodetector elements; and
   wherein the plurality of block detectors are arranged in an array such that the scintillator arrays in adjacent block detectors meet at an interface with substantially no gap therebetween and photodetectors in adjacent block detectors are separated by a gap defined by the overhang.

10. The array of block detectors as recited in claim 9, wherein the overhang is in a range of about 500 micrometers to about 600 micrometers such that the gap is in a range of about 1000 micrometers to about 1200 micrometers, respectively.

11. The array of block detectors as recited in claim 9, wherein the light guide has a beveled edge that slopes inward from the first surface to the second surface.

12. The array of block detectors as recited in claim 11, wherein the beveled edge is coated in a reflective material that reflects light inside the light guide back into the light guide.

13. The array of block detectors as recited in claim 9, wherein the bottom surface of the scintillator array has a same size and shape as the first surface of the light guide, and the active surface of the photodetector has a same size and shape as the second surface of the light guide.

14. The array of block detectors as recited in claim 9, wherein each block detector further comprises front end electronics coupled to the photodetector so as to receive data from the photodetector as electrical signals generated when light impinges on photodetector elements in the photodetector, the front end electronics having a surface area smaller than the first surface area of the light guide.

* * * * *